(12) United States Patent
Huang et al.

(10) Patent No.: US 11,896,484 B2
(45) Date of Patent: Feb. 13, 2024

(54) IMPLANT LOADING APPARATUS

(71) Applicant: SHANGHAI MICROPORT CARDIOFLOW MEDTECH CO., LTD., Shanghai (CN)

(72) Inventors: Feng Huang, Shanghai (CN); Jing Zhao, Shanghai (CN); Guoming Chen, Shanghai (CN); Yu Li, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 0 days.

(21) Appl. No.: 17/040,060

(22) PCT Filed: Jan. 11, 2019

(86) PCT No.: PCT/CN2019/071341
§ 371 (c)(1),
(2) Date: Sep. 22, 2020

(87) PCT Pub. No.: WO2019/179221
PCT Pub. Date: Sep. 26, 2019

(65) Prior Publication Data
US 2021/0015610 A1  Jan. 21, 2021

(30) Foreign Application Priority Data
Mar. 22, 2018 (CN) .............................. 201810241334

(51) Int. Cl.
*A61F 2/24* (2006.01)
(52) U.S. Cl.
CPC .................................. *A61F 2/2427* (2013.01)
(58) Field of Classification Search
CPC .............................. A61F 2/9522; A61F 2/9525
See application file for complete search history.

(56) References Cited

U.S. PATENT DOCUMENTS

2012/0290079 A1   11/2012   Murad et al.
2014/0330368 A1*  11/2014   Gloss .................... A61F 2/9525
                                                          623/2.11
(Continued)

FOREIGN PATENT DOCUMENTS

CN   104586542 A   5/2015
CN   106361467 A   2/2017
(Continued)

OTHER PUBLICATIONS

Extended European search report dated Dec. 2, 2021, in counterpart European Patent Application No. 19770259.0 (8 pages).
(Continued)

*Primary Examiner* — Shaun L David
(74) *Attorney, Agent, or Firm* — NSIP Law

(57) ABSTRACT

The present application discloses an implant loading apparatus comprising a guider and a guide base. The guider is sleeved on the exterior of the guide base. The guide base comprises a guide column, a connecting section, and a base connected in the axial direction. Fixing sections are provided on either end of the connecting section. The guide base is removably connected to the guider via the fixing sections. The guide base is provided with the two fixing sections that fit the guider to implement twice removable fixing, thus favoring a coaxial operation. A valve stent is neither twisted nor tilted during a compression process, thus increasing loading efficiency, greatly reducing the operation difficulty of a surgery, and allowing the implementation of a single person operation.

12 Claims, 4 Drawing Sheets

(56) References Cited

U.S. PATENT DOCUMENTS

2016/0278955 A1* 9/2016 Liu ..................... A61F 2/2418
2016/0346106 A1* 12/2016 Hacker ................ A61F 2/2418
2017/0231755 A1   8/2017 Gloss et al.
2017/0367821 A1* 12/2017 Landon ................ B21D 39/04

FOREIGN PATENT DOCUMENTS

EP          3 064 174 A1    9/2016
WO         2012106491 A1    8/2012
WO         2016191338 A1   12/2016
WO     WO 2016/191338 A1   12/2016

OTHER PUBLICATIONS

Japanese Office Action dated Dec. 7, 2021, in counterpart Japanese Patent Application No. 2020-551319 (7 pages in English, 5 pages in Japanese).
Japanese Office Action dated Jul. 26, 2022, in counterpart Japanese Patent Application No. 2020-551319 (4 pages in English, 3 pages in Japanese).
Japanese Office Action dated Feb. 14, 2023, in counterpart Japanese Patent Application No. 2020-551319 (2 pages in English, 1 page in Japanese).
Japanese Office Action dated Feb. 14, 2023, in counterpart Japanese Patent Application No. 2020-551319 (3 pages in English, 2 pages in Japanese).

* cited by examiner

IMPLANT LOADING APPARATUS

CROSS-REFERENCE TO RELATED APPLICATIONS

This application is a continuation of International Application No. PCT/CN2019/071341, filed on Jan. 11, 2019, which claims to the Chinese Application No. 201810241334.6, filed on Mar. 22, 2018. The disclosure of both applications are hereby incorporated by reference in their entireties.

FIELD

The present application relates to an interventional medical operation tool, in particular relates to an implant loading apparatus.

BACKGROUND

Interventional aortic valve implantation is a new minimally invasive valve replacement technology developed in recent years in the world. The principle is that the valve prosthesis is loaded into the delivery system and delivered to the aortic root via catheter. Stent release can ensure that the valve is fixed to the aortic valve ring, instead of the original valve with degraded function, so that the patient's heart function can be improved. This technique can be used to treat aortic valve disease without thoracotomy and cardiac arrest surgery. It can avoid the huge trauma caused by previous surgical thoracotomy and cardiac arrest surgery.

This technique requires compressing the valve stent to a small diameter for loading into the delivery system, which needs to deliver the valve stent to the primary annulus. However, the stent or the valve on the stent is easy to be damaged due to over compression, uneven compression or local accidental bending, which eventually leads to the functional defect or reduced service life of the stent or valve, even the valve stent cannot be implanted normally. Especially when loading the self-expanding stent, it becomes more difficult because of the tension of the self-expanding stent. In addition, a long implantation time will increase the risk of surgery. The existing patent WO2013177684A1 describes a method and equipment for loading a valve prosthesis into a delivery system, the equipment comprises a plurality of shells with different inner diameters to load a stent. And the disadvantage is that the operation is complex. Patent US2012330408a1 describes a cardiac valve loading apparatus, in which the compression element is connected by rotation fixation, and the valve stent is easy to be damaged due to torsion and tilt during compression.

On the other hand, the catheter of the delivery system is very long, and the whole delivery system is very large. When using the traditional loading tool to load the stent, one person needs to fix the loading tool with stent at one end and another person needs to operate the handle at the other end, so at least two people, or even more people need to cooperate to complete the whole loading process. And when the valve is compressed to a certain extent, the valve leaflets need to be sorted out, and then follow-up operation can be carried out. It is difficult to grasp the timing of sorting the valve leaflets because the handle and loading tool are operated by different people, which depends on the communication between operators, or fully rely on the experience of the handle operator. But the handle operator can't see the pressing and holding condition of the stent at the other end, and often makes inaccurate judgment.

Therefore, a loading apparatus with simple operation, high loading efficiency and single person operation is needed.

SUMMARY

The problem to be solved by the present application is to provide a new implant loading apparatus, to solve the problem that the stent is easy to twist, tilt or even damage in the process of valve stent compression, to improve the loading efficiency and reduce the operation difficulty of the operator.

Embodiments of the present application is to solve the above problems is to provide an implant loading apparatus, and comprising a guider and a guide base, the guider is sleeved on the exterior of the guide base, the guide base comprises a guide column, a connecting section and a base connected in the axial direction, fixing sections are provided on either end of the connection section, the guide base is removably connected to the guider via the fixing sections.

Further, the fixing section close to the guide column is a first fixing section, and the fixing section close to the base is a second fixing section; the guider comprises a fixing area, the fixing area is clamped with the first fixing section or the second fixing section, so that the guide base can be removably connected to the guider; a main compression area is provided on the inner surface of the guider to compress the implant.

Further, a bayonet is provided on the fixing area, the bayonet is clamped with the first fixing section or the second fixing section.

Further, the number of the bayonet is at least two, and the at least two bayonets are symmetrically distributed in the circumferential direction of the guider.

Further, the bayonet in the part of the fixing area is provided with an inward bulge.

Further, a connection area is provided between the main compression area and the fixing area, the connection area is cylindrical, and the diameter of the connection area is the same as the diameter of the inlet end of the main compression area.

Further, two symmetrical and axially extending gaps are provided on the left and right edges of the bayonet, the length of the gaps is greater than or equal to the length of the fixing area, and less than the sum of the length of the connection area and the fixing area.

Further, the length of the gaps ranges from 1-25 mm.

Further, an auxiliary compression area through an inner cavity is provided on the guide base, the auxiliary compression area is a funnel-shaped space formed by a rotary body, and the diameters of the two end faces of the rotary body are different.

Further, a groove is provided on the surface of the guide base, the groove is located between the guide column and the fixing section.

Further, the ratio range of the inner diameter of the groove to the diameter of the tail of the implant is 1:1-2:1, and the width range of the groove is 1-5 mm.

Further, the first fixing section is in the shape of a circular platform, and the diameter of the bottom of the circular platform is slightly larger than the diameter of the connecting section.

Further, the second fixing section is cylindrical, and the diameter of the second fixing section is slightly smaller than the diameter of the connecting section.

Further, the connecting section is cylindrical, and the diameter of the connecting section is slightly smaller than the diameter of the inlet end of the main compression area.

Further, the outer surface of the connecting section is provided with a groove track which is axially connected with the first fixing section and the second fixing section and matched with the bayonet, and the number of the groove track is the same as the number of the bayonet.

Further, the ratio of the height of the guide column to the height of the guider ranges from 0.6:1-2:1.

The present application has the following beneficial effects compared with the prior art: the guide base of the loading apparatus provided by the present application has two fixing sections, which can realize two removable fixation with the guider, and is convenient for coaxial operation. The valve stent will not twist or tilt in the compression process, which improves the loading efficiency, greatly reduces the difficulty of the operation, and can realize single person operation. In one embodiment, the first fixation is convenient for the operator to adjust the relative position of the lug and the fixing lug, avoiding the possible twisting or tilting of the valve stent, so that the valve stent can be loaded into the delivery system in a more accurate state; the second fixation is convenient for the operator to operate the handle of the delivery system, and according to the signals of popping of the guide base and the guider, the valve leaflets can be tidied at a suitable time and further compression loading is completed without multiple round-trip observation between the two ends of the delivery system, which significantly improves the loading efficiency. In addition, the connecting section of the guide base also plays the role of coaxial guidance to prevent the implant from twisting or tilting in the compression process; the design of the bayonet of the guide is flexible which is convenient for coaxial operation, and the bulge is convenient for clamp fixation with the guide base.

BRIEF DESCRIPTION OF FIGURES

FIG. 4b is a schematic view illustrating the sectional structure of FIG. 4a.

FIG. 5b is a schematic view illustrating the sectional structure of FIG. 5a.

In the figures:
1—guider 2—guide base 3—valve stent 4—delivery system 11—an outlet area 12—a second compression area 13—a first compression area
14—a connection area 15—a fixing area 16—a bayonet 161—a gap 162—a bulge 21—a guide column 22—a first fixing section 23—a connecting section
24—a second fixing section 25—a base 26—an auxiliary compression area 27—a groove 28—a groove track 31—an outflow channel 32—an inflow channel 33—a lug
41—a fixing lug 42—an inner pipe 43—an outer pipe

DETAILED DESCRIPTION

The present application will be further described in combination with the accompanying drawings and embodiments. To facilitate the description of the present application, the term "or" is generally used to include the meaning of "and/or", unless the content otherwise expressly indicates.

Figure 1:
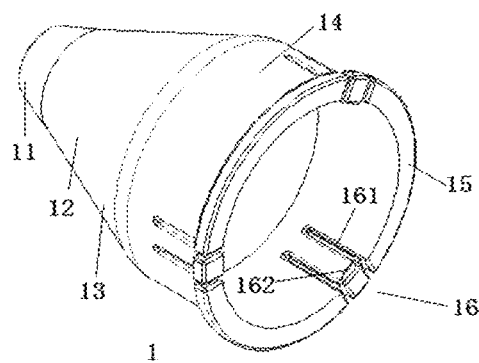
FIG. 1 is a schematic view illustrating the structure of the guider according to one embodiment of the present application.
Figure 2:
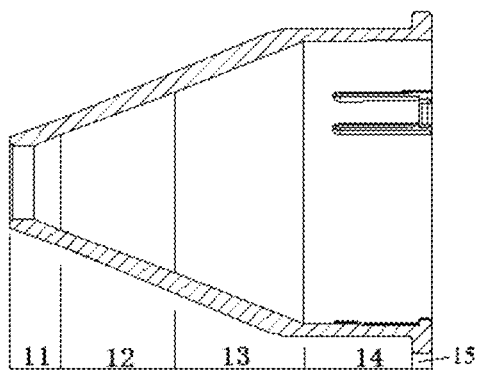
FIG. 2 is a schematic view illustrating the section of the guider according to one embodiment of the present application.
Figure 4A:
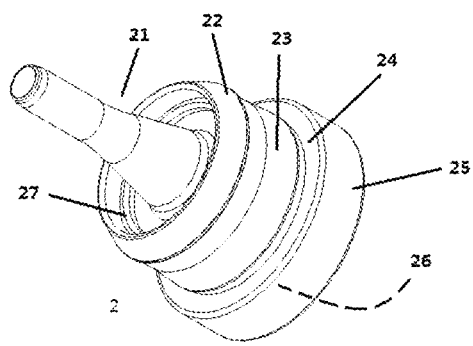
FIG. 4a is a schematic view illustrating the structure of the guide base according to one embodiment of the present application.
Figure 4B:
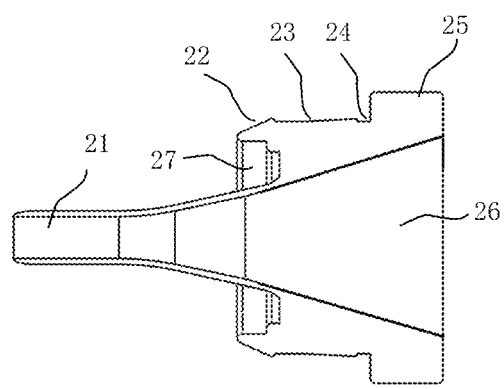

FIG. 1 is a schematic view illustrating the structure of the guider according to one embodiment of the present application. FIG. 2 is a schematic view illustrating the section of the guider according to one embodiment of the present application. FIG. 4a is a schematic view illustrating the structure of the guide base according to one embodiment of the present application. FIG. 4b is a schematic view illustrating the sectional structure of FIG. 4a.

As shown in FIG. 1, FIG. 2, FIG. 4a and FIG. 4b, the implant loading apparatus provided by the present application comprising a guider 1 and a guide base 2, the guider 1 is sleeved on exterior of the guide base 2, the guide base 2 comprises a guide column 21, a connecting section 23 and a base 25, a main compression area is provided on the inner surface of the guider 1 to compress the implant. The guider 1 and the guide baser 2 can slide relative to each other along the extension direction of the guide column 21, and the two ends of the connecting section 23 are respectively formed with a fixing section which can be connected with the guider 1. Preferably, the main compression area is divided into a first compression area 13 and a second compression area 12.

The implant of the present application uses a valve stent as an example to explain the present application, but the valve stent is not a limitation of the implant. Valve stents, such as cardiac valve stents, can be provided for transcatheter implantation. Although the present embodiment illustrates a common valve stent geometry, the present application is not limited to any particular valve stent geometry.

Figure 6:
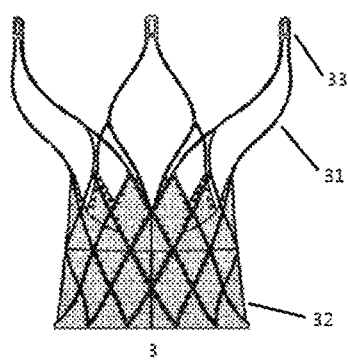
FIG. 6 is a schematic view illustrating the structure of the valve stent in the stretched state according to one embodiment of the present application.

As shown in FIG. 6, the valve stent 3 comprises an inflow channel 31, an outflow channel 32 and a lug 33, the valve stent 3 is loaded into the delivery system through the loading apparatus, transported into the human body by the delivery system catheter under the contraction state to the target area, and then released to the state as shown in FIG. 6. The present application has no special restriction on the manufacturing material of the valve stent, which can be any existing material in the art, preferably adopting the shape memory alloy material.

The guider 1 of the present application comprises an outlet area 11, a second compression area 12, a first compression area 13, a connection area 14 and a fixing area 15, there is a bayonet 16 at the fixing area, as shown in FIG. 1 and FIG. 2. The diameter of the inlet end of the first compression area 13 is larger than the diameter of the outlet end of the second compression area 12. When loading, the first compression area 13 initially compresses the valve stent. At this time, the second compression area 12 can maintain a certain opening diameter of the outflow channel 31 of the valve stent 3, so that the operator can install the stent to the fixing head of the delivery system and maintain the relative position with the fixing head. The first compression area 13 and the second compression area 12 are spaces defined by the inner surface of the guider, the inner surface is a rotating surface, and the bus of the rotating surface is a straight line or curve. Preferably, the bus of the inner surface of the second compression area 12 is a curve, which can better maintain the opening diameter of the outflow channel 31 of the valve stent 3. The outlet end of the second compression area 12 of the guider 1 is provided with an outlet area 11 to facilitate the entry of the inner pipe 5 of the delivery system and the extension of the outflow channel 31 of the valve stent 3. The outlet area 11 is a space defined by the inner surface of the guider, the inner surface is a rotating surface, and the bus of the rotating surface is a straight line. The guider 1 also comprises a connection area 14 and a fixing area 15 connected with the inlet end of the first compression area 13. Through the connection area 14 and the fixing area 15, the guider 1 and the guide base 2 can be removably connected. The connection area 14 is cylindrical with a diameter equal to the diameter of the inlet end of the first compression area 13. The fixing area 15 is located at the inlet end of the connection area 14 and the outer diameter of the fixing area 15 is larger than the outer diameter of the connection area 14. A bayonet 16 is provided in the connection area 14 and the fixing area 15. The height of the bayonet 16 along the axial direction of the guider 1 is larger than the height of the fixing area 15, and smaller than the sum of the height of the connection area 14 and the fixing area 15. The height of the bayonet 16 is 1-25 mm. The bayonet 16 can be rectangular, semicircular, arched, spherical, etc. the number of the bayonets can be 2, 3 or more, which are symmetrically distributed in the circumferential direction of the guider 1, which can be axisymmetric, centrosymmetric or rotationally symmetric, preferably centrosymmetric distribution.

Figure 3:
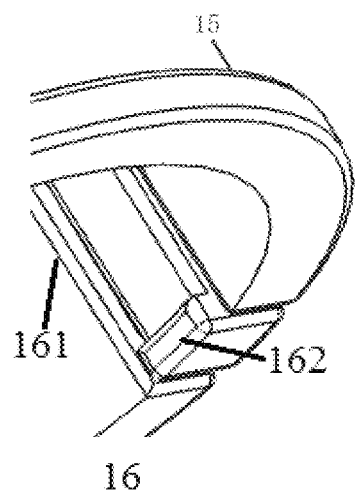
FIG. 3 is an enlarged schematic view illustrating the structure of the bayonet on the fixing area of the guider in FIG. 1.

The left and right edges of the bayonet 16 of the guider 1 of the present application are provided with two symmetrical and axially extended gaps 161, the height of which is the same as that of the bayonet 16, as shown in FIG. 1 and FIG. 2. The shape of the gap 161 can be rectangular, zigzag, wavy, circular, trapezoid, square or polygon, etc. The design of the gap 161 makes the bayonet 16 elastic, which is more conducive to the connection and fixation of the guider and the guide base. The bayonet 161 has an inward bulge 162 in the fixing area, as shown in FIG. 3, which is used for the buckle connection with the guide base 2.

As shown in FIG. 4a and FIG. 4b, the guide base 2 comprises a base 25 and a funnel-shaped guide column 21 provided on the base 25. The inner cavity of the guider 1 can accommodate the guide column 21. The height ratio of the guide column. 21 to the height of the guider 1 ranges from 0.6:1-2:1. The diameter of one end of the guide column. 21 connected with the base 25 is larger than that of the other end. The guide base 2 is provided with the auxiliary compression area 26 defined by the through inner cavity, which can accommodate the inner pipe 5 of the delivery system. In one embodiment of the present application, the auxiliary compression area 26 is a funnel-shaped space, the surface of the funnel-shaped space can be the surface formed by the rotary body, and the diameters of the two end faces of the rotary body are different, and the bus of the rotary body can be a straight line or a curve. In other embodiments of the present application, the auxiliary compression region 26 may also be in the shape of a circular platform, a spherical gap or a spherical crown, and may also be a combination of surfaces formed by a plurality of the above-mentioned rotary body. When the valve stent 3 is loaded, the auxiliary compression area 26 can pre-compress the inflow channel 32 of the valve stent 3, which is helpful for loading. On the base 25 of the guide base 2, and on the periphery of the guide column 21, the first fixing section 22, the connection section 23 and the second fixing section 24 are successively arranged along the axial direction of the guide base 2, which are used for clamp connection with the connection area 14 and the fixing area 15 of the guider 1.

The present application can also provide a groove 27 on the surface of the base 25 of the guide base 2 in a circumferential direction, and the groove 27 is located between the guide column 21 and the first fixing section 22. The inner diameter of the groove 27 should be slightly larger than that of the valve stent inflow channel 32. Preferably, the ratio of the inner diameter of the groove 27 to the diameter of the tail of the valve stent 3 (i.e. the end of the inflow channel on the valve stent 3) is 1:1-2:1, and the width of the groove 27 is 1-5 mm. When the guide base 2 is used to compress the valve stent 3, the groove 27 is made to accommodate the inflow channel 32 of the valve stent 3 which can further reduce the probability of torsion and inclination of the valve stent 3 during the compression process.

Figure 5A:
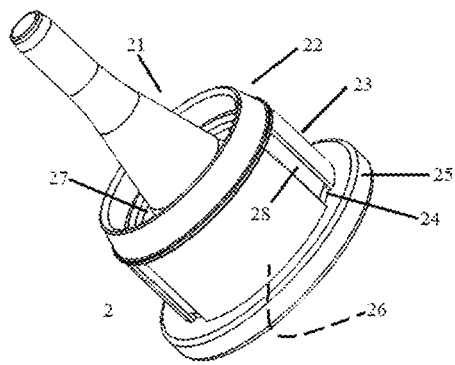
FIG. 5a is a schematic view illustrating the structure of the guide base with a groove track according to one embodiment of the present application.
Figure 5B:
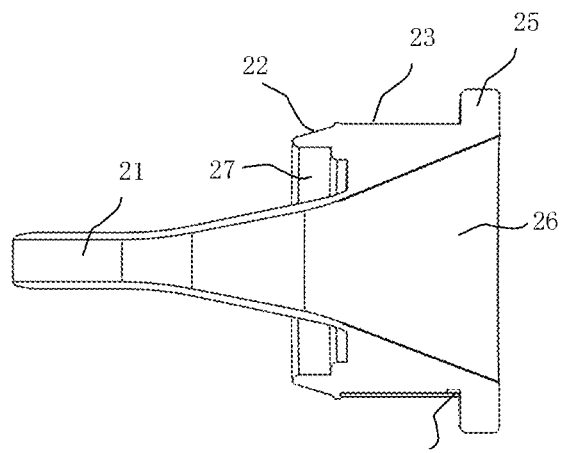

The connecting section 23 on the guide base 2 of the present application is cylindrical. The outer surface of the connecting section 23 may be a smooth surface, a frosted surface, etc. Preferably, the outer surface of the connecting section 23 is provided with a groove track 28 along the axial direction. As shown in FIG. 5a and FIG. 5b, the number of the groove track 28 is the same as that of the bayonet 16 on the guider 1. The bayonet 16 is matched with the groove track 28 and moves along the direction of the groove track 28, which is more convenient for the removable connection between the guider 1 and the guide base 2.

Figure 7:
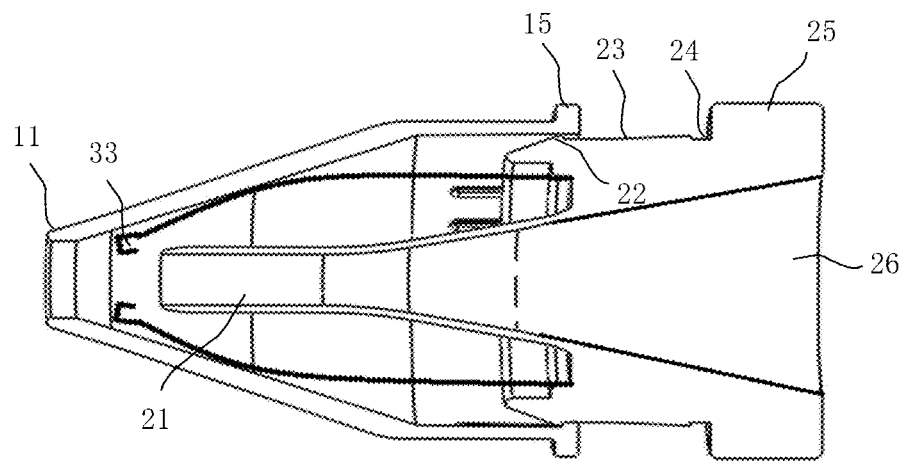
FIG. 7 is a schematic view illustrating the first fixation of the guider and the guide base according to one embodiment of the present application.
Figure 8:
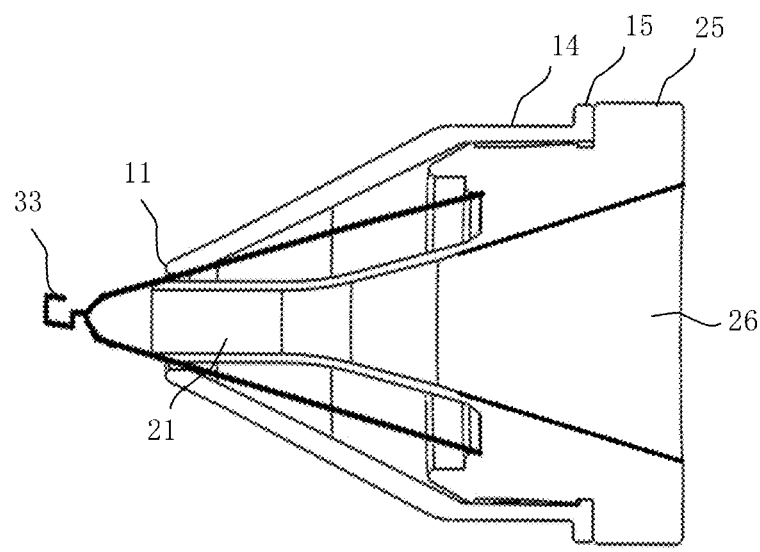
FIG. 8 is a schematic view illustrating the second fixation of the guider and the guide base according to one embodiment of the present application.
Figure 9:
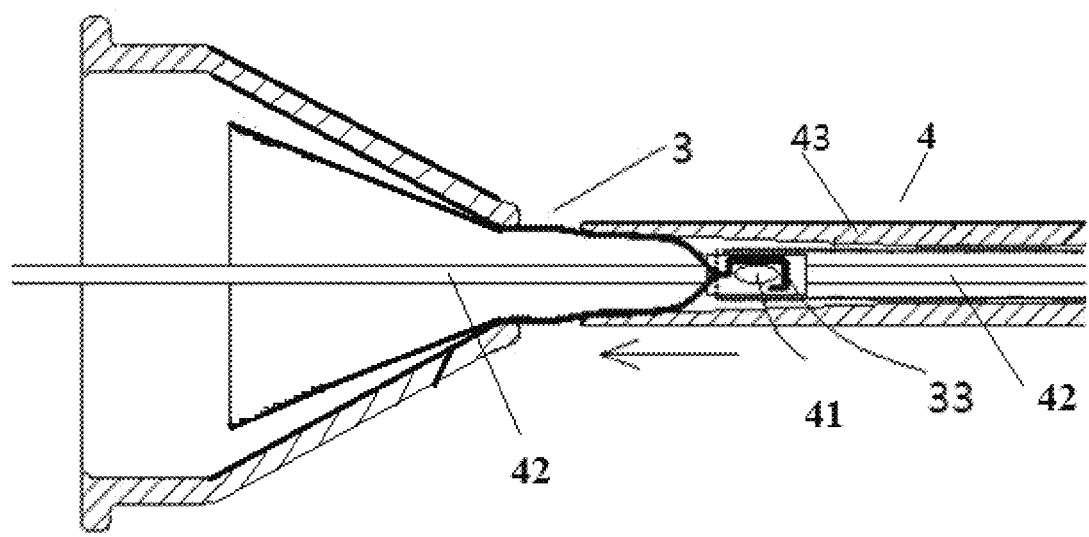
FIG. 9 is a schematic diagram illustrating the loading apparatus loading the stent according to one embodiment of the present application.

The guide base 2 of the present application is connected with the connecting area 14 and the fixing area 15 of the guider 1 by the first fixing section 22, the connecting section 23 and the second fixing section 24 in a clamp type removable way. The first fixing section 22 of the guide base 2 is in the shape of a circular platform, and the diameter of the lower bottom of the circular platform is slightly larger than the diameter of the connecting section 23. The first fixing section 22 can be engaged with the bayonet 16 of the guider 1 to form a removable first fixing, as shown in FIG. 7. At this time, the valve stent 3 changes from the expansion state to the first compression state, and the diameter of the head end of the valve stent 3 (i.e. the end where the lug 33 of the valve stent 3 is located) in the first compression state is obviously smaller than the diameter of its expansion state. The connecting section 23 of the guide base 2 is cylindrical. After the guider 1 is fixed for the first time, it can move along the connecting section 23 to the second fixing section 24. The connecting section 23 plays the role of coaxial guidance. The second fixing section 24 of the guide base 2 is cylindrical, and the diameter of the second fixing section 24 is slightly smaller than the diameter of the connecting section 23. The second fixing section 24 can be engaged with the bayonet 16 of the guider 1 to form a removable second fixing, as shown in FIG. 8. At this time, the valve stent 3 changes from the first compression state to the second compression state. The diameter of the head end of the valve stent 3 (i.e. the end where the lug 33 of the valve stent 3 is located) in the second compression state is obviously smaller than its diameter in the first compression state, and even the valve stent is conical, to facilitate loading the valve stent 3 into the outer pipe 43 of the delivery system 4 of the valve stent 3 whose diameter is significantly smaller than that in the expanded state. This coaxial guided two-time fixation method can avoid twisting and tilting of valve stent 3 during compression. As shown in FIG. 7, FIG. 8 and FIG. 9, when the valve stent 3 is loaded into the delivery system 4 by the loading apparatus of the present application, the outer pipe 43 of the delivery system is first withdrawn to expose the fixing lug 41 on the inner pipe 42, and the inner pipe 42 passes through the guider 1 from the outlet area 11 to the fixing area 15. Then, the tail of the valve stent 3 is placed in the groove 27 of the guide base 5, and the inner pipe 42 passes through the auxiliary compression area 26 of the guide base 2 from the guide column 11 to the base 25. Push the guider 1 of the guide base 2 gently, so that the guider 1 is sleeved on exterior of the guide base 2. In this process, the outflow channel 31 of the valve stent 3 successively enters the first compression area 13 and the second compression area 12. When it reaches the second compression area 12, the valve stent 3 is in the first compression state, as shown in FIG. 7. At this time, the fixing area 15 of the guider 1 is fixed with the first fixing section 22 of the guide base 2 through the bayonet 16. Because of the first fixation of the guider 1 and the guide base 2, they form a relatively stable combination state, and the valve stent 3 can maintain the first compression state for a long time without external force. After the first fixation, the operator can adjust the relative position between the lug 33 of the valve stent 3 and the fixing lug 41 of the delivery system 4 by turning the guider 1 and the guide base 2 as a whole, to fix the lug 33 on the fixing lug 41 in the next step. The first fixation frees the operator's hands, the operator does not need to hold the guider and the guide base with hands to maintain the relative position of the two. It is more convenient to adjust the position of the lug 33 and the fixing lug 41. Moreover, the relative position of the valve stent 3 and the guider 1 and the guide base 2 is also fixed, without torsion. In addition, when the valve stent 3 enters the second compression region 12, the guide column 21 of the guide base 2 can maintain a proper compression ratio at the end of the outflow channel 31, to prevent the outflow channel 31 from being deformed due to excessive compression, so that the lug 33 cannot be well matched with the fixing lug 41 of the delivery system 4.

Then, the guider 1 of the guide base 2 is further pushed forward, and the guider 1 moves along the connecting section 23 of the guide base 2 to the second fixing section 24 until the fixing area 15 of the guider 1 is occluded with the second fixing section 24 through the bayonet 16, the valve stent 3 is in the second compression state, and the lug 33 of the valve stent 3 is penetrated from the outlet area 11 of the guider 1, as shown in FIG. 8. At this time, the guider 1 and the guide base 2 are fixed for the second time. The operator can release his hands again, further fine tune the relative positions of the lug 33 and the fixing lug 41, and make the lug 33 accurately fixed to the fixing lug 41 of the delivery system 4, as shown in FIG. 9. After that, the operator can operate the handle at the other end of the delivery system 4, so that the valve stent 3 is gradually pressed and loaded into the outer pipe 43 of the delivery system 4. Due to the large tension of the valve stent 3, the elastic design of the bayonet 16 of the guider can make the guider 1 automatically pop open from the second fixing section 24 of the guide base 2, but the first fixing section 22 will play a blocking role, to ensure that The guider 1 does not disengage from the guide base 2. When the operator finds that the guider 1 has popped open, he can stop the handle and go back to the loading apparatus to arrange the valve leaflets. After the valve leaflets is arranged, the guide base 2 can also be removed from the delivery system 4 for reverse use, i.e. the inner pipe 42 of the delivery system 4 passes through the auxiliary compression area 26 of the guide base 2 from the direction of the guide column 21 of the base 25, and the reverse guide base 2 is pushed in the direction of the guider 1, the inflow channel 32 of the stent is further compressed by the auxiliary compression area 26, and finally the handle of the delivery system 4 is operated until the completion of loading the whole valve stent 3.

The guider 1 and guide base 2 in the loading apparatus of the present application can be made of transparent plastic material suitable for medical apparatus. Of course, other transparent or non-transparent materials can also be used. Preferably, a loading apparatus made of a transparent material helps the operator to observe the condition of the valve stent 3 and the delivery system inside during loading.

In a summary, the loading apparatus provided in the present application, after the implant is loaded between the guider and the guide base, the guider and the guide base are removably fixed twice in the process of mutual propulsion. After the first fixation, the operator's hands can be freed, and it is convenient for the operator to operate the loading apparatus and the delivery system, so that the implant can be loaded into the delivery system in a more accurate state. At the same time, the relative position of the implant and the guider and the guide base is fixed without torsion. When the guider and the guide base are transited from the first fixation to the second fixation, the connection section of the guide base plays the role of coaxial guidance to prevent the implant from torsion or inclination during the compression process. The design of the guide bayonet in the present application is flexible which is convenient for coaxial operation, and the bayonet has a bulge, which is used for clamp fastening with the guide base. When loading the implant, when the lug is fixed on the fixing lug of the delivery system, the operator can release his hands to operate the handle at the other end. With the outer pipe of the delivery system advancing towards the implant, due to the high tension of the implant, the elastic design of the guide bayonet can make the guider automatically pop open from the second fixing section of the guide base, but the first fixing section will play a blocking role, and the guider will not break away from the guide base. The operator can stop the handle after finding that the guider popping open, to facilitate the arrangement of the valve leaflets and the subsequent loading. Although the present application has been disclosed as above in a preferred embodiment, it is not used to define the present application.

What is claimed is:

1. An implant loading apparatus, comprising:
a guider and a guide base,
wherein the guider is sleeved on an exterior of the guide base, the guide base comprises a guide column, a connecting section and a base connected in an axial direction, a fixing section is provided on each end of the connecting section, and the guide base is removably connected to the guider via the fixing section, and
wherein the fixing section close to the guide column is a first fixing section, and the fixing section close to the base is a second fixing section; the guider comprises a fixing area and a bayonet is provided on the fixing area, the bayonet in a part of the fixing area is provided with a radially inward bulge, two symmetrical and axially extending gaps are provided on left and right edges of the bayonet, a length of each of the gaps is greater than or equal to a length of the fixing area, and less than a sum of lengths of the connection area and the fixing area, the bayonet is clampable with the first fixing section and the second fixing section respectively, such that the guide base can realize two respective removable connections with the guider, and a main compression area is provided on an inner surface of the guider to compress an implant.

2. The implant loading apparatus according to claim 1, wherein the number of the bayonet is at least two, and at least two bayonets are symmetrically distributed in a circumferential direction of the guider.

3. The implant loading apparatus according to claim 1, wherein a connection area is provided between the main compression area and the fixing area, the connection area is cylindrical, and the diameter of the connection area is the same as the diameter of an inlet end of the main compression area.

4. The implant loading apparatus according to claim 1, wherein the length of the gaps ranges from 1-25 mm.

5. The implant loading apparatus according to claim 1, wherein an auxiliary compression area through an inner cavity is provided on the guide base, the auxiliary compression area is a funnel-shaped space formed by a rotary body, and the diameters of two end faces of the rotary body are different.

6. The implant loading apparatus according to claim 1, wherein a groove is provided on the surface of the guide base, the groove is located between the guide column and the fixing section.

7. The implant loading apparatus according to claim 6, wherein a ratio range of an inner diameter of the groove to the diameter of a tail of the implant is 1:1-2:1, and the width range of the groove is 1-5 mm.

8. The implant loading apparatus according to claim 1, wherein the first fixing section is in the shape of a circular platform, and the diameter of a bottom of the circular platform is slightly larger than the diameter of the connecting section.

9. The implant loading apparatus according to claim 1, wherein the second fixing section is cylindrical, and the diameter of the second fixing section is slightly smaller than the diameter of the connecting section.

10. The implant loading apparatus according to claim 1, wherein the connecting section is cylindrical, and the diameter of the connecting section is slightly smaller than the diameter of an inlet end of the main compression area.

11. The implant loading apparatus according to claim 10, wherein an outer surface of the connecting section is provided with a groove track which is axially connected with the first fixing section and the second fixing section and matched with the bayonet, and the number of the groove track is the same as the number of the bayonet.

12. The implant loading apparatus according to claim 1, wherein the ratio of the height of the guide column to the height of the guider ranges from 0.6:1-2:1.

* * * * *